US010319091B2

United States Patent
Hoffmann et al.

(10) Patent No.: US 10,319,091 B2
(45) Date of Patent: Jun. 11, 2019

(54) PROVIDING IMAGE SUPPORT TO A PRACTITIONER

(71) Applicants: Thomas Hoffmann, Madgeburg (DE); Martin Skalej, Magdeburg (DE)

(72) Inventors: Thomas Hoffmann, Madgeburg (DE); Martin Skalej, Magdeburg (DE)

(73) Assignee: Siemens Healthcare GmbH, Erlangen (DE)

( * ) Notice: Subject to any disclaimer, the term of this patent is extended or adjusted under 35 U.S.C. 154(b) by 270 days.

(21) Appl. No.: 15/368,670

(22) Filed: Dec. 4, 2016

(65) Prior Publication Data

US 2017/0161897 A1    Jun. 8, 2017

(30) Foreign Application Priority Data

Dec. 4, 2015   (DE) .................. 10 2015 224 356

(51) Int. Cl.
| | |
|---|---|
| *G06K 9/00* | (2006.01) |
| *G06T 7/00* | (2017.01) |
| *G06T 7/11* | (2017.01) |
| *A61B 6/00* | (2006.01) |
| *G06T 7/60* | (2017.01) |

(52) U.S. Cl.
CPC .......... *G06T 7/0012* (2013.01); *A61B 6/4441* (2013.01); *A61B 6/461* (2013.01);
(Continued)

(58) Field of Classification Search
CPC ....... A61B 6/4441; A61B 6/461; A61B 6/487; A61B 6/504; A61B 6/5235; A61B 6/5252;
(Continued)

(56) References Cited

U.S. PATENT DOCUMENTS

| | | |
|---|---|---|
| 2008/0212857 A1 | 9/2008 | Pfister et al. |
| 2011/0019890 A1 | 1/2011 | Oikawa |

(Continued)

FOREIGN PATENT DOCUMENTS

| | | |
|---|---|---|
| DE | 102006045423 A1 | 4/2008 |
| DE | 102011078220 A1 | 8/2012 |

(Continued)

OTHER PUBLICATIONS

Davis, B., et al. "4D digital subtraction angiography: implementation and demonstration of feasibility." American Journal of Neuroradiology (2013). (Year: 2013).*

(Continued)

*Primary Examiner* — Nirav G Patel
(74) *Attorney, Agent, or Firm* — Lempia Summerfield Katz LLC

(57) ABSTRACT

A three-dimensional subtraction angiography image data set including a target region of the patient is acquired. A region of interest is selected. An imaging geometry is defined for monitoring the intervention using an X-ray device. The image-obscuring blood vessels that superimpose the region of interest in the imaging geometry and imaging zones that show fractions of the image-obscuring blood vessels in the imaging geometry are determined. Path information relating to the image-obscuring blood vessels is defined. The information relating to the path is input into a two-dimensional forward projection data set. A fluoroscopic image is acquired in the imaging geometry. Pixels showing the image-obscuring blood vessels in the fluoroscopic image are determined using the path information and image intensity information from the fluoroscopic image. A masked image of the image-obscuring blood vessels is subtracted. The fluoroscopic image that has been modified is displayed.

16 Claims, 2 Drawing Sheets

(52) U.S. Cl.
CPC .............. *A61B 6/487* (2013.01); *A61B 6/504* (2013.01); *A61B 6/5235* (2013.01); *A61B 6/5252* (2013.01); *G06T 7/11* (2017.01); *G06T 7/60* (2013.01); *G06T 2207/10021* (2013.01); *G06T 2207/10064* (2013.01); *G06T 2207/30101* (2013.01); *G06T 2211/404* (2013.01)

(58) Field of Classification Search
CPC . G06T 2207/10021; G06T 2207/10064; G06T 2207/30101; G06T 2211/404; G06T 7/0012; G06T 7/11; G06T 7/60
See application file for complete search history.

(56) References Cited

U.S. PATENT DOCUMENTS

| | | |
|---|---|---|
| 2013/0116551 A1 | 5/2013 | Florent et al. |
| 2014/0228678 A1* | 8/2014 | Meyer ..................... A61B 6/12 600/424 |
| 2015/0164605 A1 | 6/2015 | Patwardhan et al. |
| 2015/0213600 A1 | 7/2015 | Kyriakou |
| 2016/0302757 A1 | 10/2016 | Pizaine et al. |

FOREIGN PATENT DOCUMENTS

| | | |
|---|---|---|
| DE | 102011083686 A1 | 4/2013 |
| WO | WO2015075047 A1 | 5/2015 |

OTHER PUBLICATIONS

German office Action for related German Application No. 10 2015 224 356.7 dated Sep. 21, 2016, with English Translation.
European Search Report for related European Application No. 16197861.4 dated May 4, 2017.

\* cited by examiner

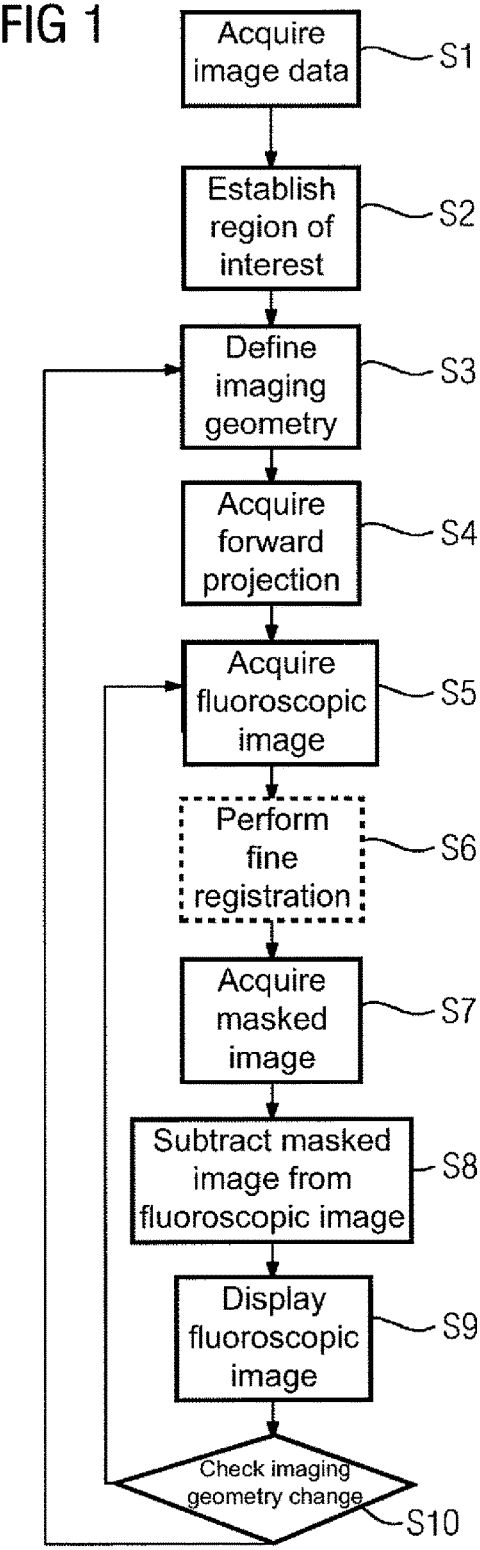

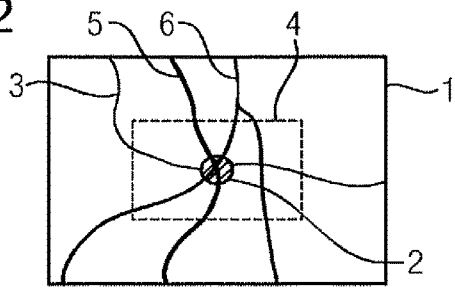
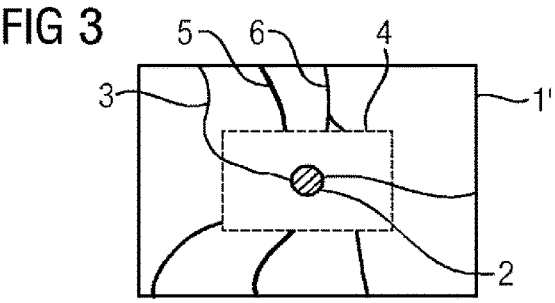
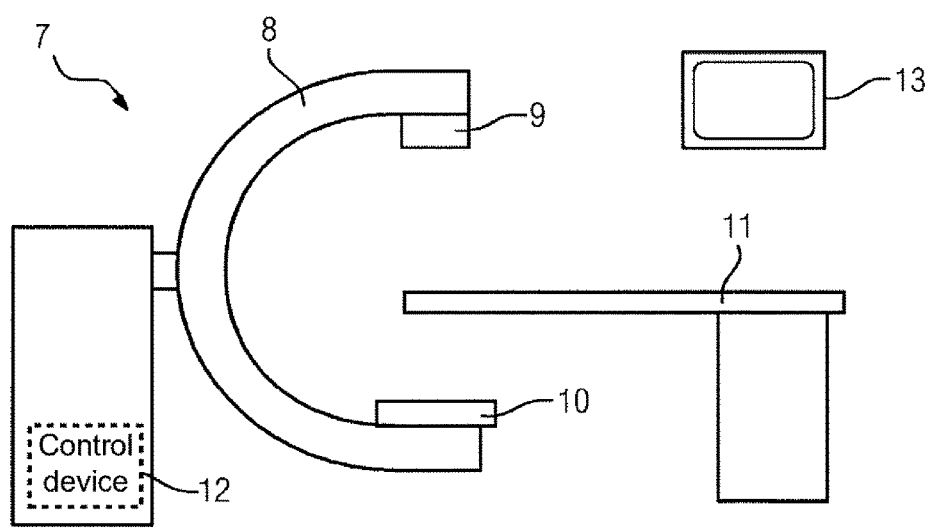

PROVIDING IMAGE SUPPORT TO A PRACTITIONER

This application claims the benefit of DE 10 2015 224 356.7, filed on Dec. 4, 2015, which is hereby incorporated by reference in its entirety.

BACKGROUND

The present embodiments relate to providing image support to a practitioner in an interventional treatment of a target area in a patient.

Minimally invasive interventions with medical instruments, such as catheters, open up new possibilities that are easier for the patient to endure for the treatment of pathologies/lesions, such as aneurysms, for example. In order to be able to monitor the path of the medical instrument and/or the progression of treatment, it has already been suggested that interventional (e.g., minimally invasive procedures) may be carried out with image monitoring. For this purpose, fluoroscopy is generally used, which provides that X-ray images are taken with an X-ray device, for which a rather lower dose of X-rays is selected.

A further important aid to image support in an interventional procedure in the patient's vascular system is subtraction angiography. This involves a contrast agent that is clearly visible in the X-ray image being administered into the patient's circulation. By subtraction of a masked image acquired without contrast agent from an X-ray image with at least some blood vessels filled with contrast agent (e.g., a contrast-filled image), a subtraction angiogram that shows only the regions filled with contrast agent (e.g., the blood vessels) may be obtained. If projection images are acquired in various projection directions and methods of reconstruction are used, in the context of subtraction angiography, a three-dimensional subtraction angiography image (e.g., a three-dimensional subtraction angiography data set) may be obtained, and therefore, a three-dimensional image of the patient's vascular system may be obtained. Such three-dimensional image data sets may be used, for example, in the context of the navigation of medical instruments when for example, the three-dimensional subtraction angiography data set is registered with the system of coordinates of a position-defining device for the medical instrument.

Using subtraction angiography in fluoroscopic monitoring is likewise known. This likewise involves a masked image acquired without contrast agent being subtracted from an X-ray image taken using contrast agent (e.g., a filled image) in order to ultimately obtain the fluoroscopic image that is to be used for monitoring.

Problems always occur with fluoroscopic image monitoring of an interventional procedure when various blood vessels in the two-dimensional subtraction angiogram in the zone around the target area (e.g., the pathological feature) are superimposed, which may not generally be avoided, however. In order to be able to estimate the target area correctly, the person carrying out the intervention changes the projection direction, which in some cases may lead to important parts of the pathological feature no longer being shown with sufficient accuracy. Therefore, it is not possible to avoid a compromise, as far as the selection of the imaging geometry and consequently of the projection direction is concerned. The problem with superimpositions is, for example, that the allocation of blood vessels is not clear. If the target area is, for example, an aneurysm that is to be treated, in a blood vessel that is likewise to be seen in the two-dimensional projection image, it is not clear whether this blood vessel originates from the aneurysm or is not in contact with the aneurysm at all.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a superimposition-free view of the target region for image monitoring of an interventional (e.g., a minimally invasive procedure irrespective of the choice of projection direction) is provided.

A method is provided, according to one or more of the present embodiments, for image support of a practitioner in the interventional treatment of a target area of a target region of a patient. The method includes arranging the acquisition of a three-dimensional subtraction angiography data set for a target region of the patient that includes the target area. A region of interest in the three-dimensional subtraction angiography data set that includes the target area is selected. An imaging geometry that implements a projection direction for acquiring two-dimensional fluoroscopic images for monitoring the intervention using an X-ray device is defined. The image-obscuring blood vessels that superimpose the region of interest in the imaging geometry and imaging zones that show portions of the image-obscuring blood vessels in the imaging geometry without superimposition by other blood vessels are acquired by forward projection of the subtraction angiography data set in the projection direction. Path information relating to the blood vessels is defined at least in the zone around the region of interest and in the imaging zones, and the path information is input into a two-dimensional forward projection data set. A fluoroscopic image is acquired in the imaging geometry. The pixels that show the image-obscuring blood vessels in the fluoroscopic image are determined by the path information, and image intensity information is acquired from the intensities measured on the pixels in the fluoroscopic image. A masked image of the image-obscuring blood vessels acquired using the path information in the region of interest and the image intensity information is subtracted from the fluoroscopic image in the region of interest. The fluoroscopic image that has been modified in this way is displayed.

The fluoroscopic image may be a monitoring image from the two-dimensional subtraction angiography in order to achieve an optimal comparability between the three-dimensional subtraction angiography data set and the two-dimensional fluoroscopic image. This provides that the acquisition of the two-dimensional fluoroscopic image includes the measurement of a filled image in the imaging geometry and the subtraction of a masked image likewise acquired in the imaging geometry. The interventional procedure may, for example, be a minimally invasive intervention in the patient's vascular system (e.g., in the brain and/or heart region).

The basic concept underlying one or more of the present embodiments is using the background information provided by the three-dimensional subtraction angiography data set in order to identify, for the last selected imaging geometry, image-obscuring blood vessels that appear as superimposed in the projection and to further use the background information from the three-dimensional subtraction angiography data set in order to allow an estimation of the attenuation fractions to these image-obscuring blood vessels in the region of interest. The estimation may be used for data correction in the region of interest. This is because, if the projection directions and the positions of the X-ray source are known, it is then easy to identify imaging zones in which the image-obscuring blood vessel appears without being superimposed by other structures (e.g., blood vessels) if an image is acquired in the imaging geometry. If these imaging zones are again found in the fluoroscopic image, then it may be assumed there that the intensity measured (e.g., the image value) was essentially generated only by the attenuation due to the image-obscuring blood vessel. Conclusions may be drawn therefrom about the attenuation of the image-obscuring blood vessel in the region of interest, such that a masked image may be created for the region of interest. The masked image contains only the image-obscuring blood vessels and therefore the blood vessels and the attenuated fractions thereof in the measured intensity. If this masked image is subtracted from the fluoroscopic image, the image-obscuring blood vessels are therefore removed due to the removal of attenuated fractions, and a modified fluoroscopic image, in which the target region is not superimposed as through a window and may be clearly identified, is generated.

It is therefore possible using the method according to one or more of the present embodiments to provide to an observer in any technically available imaging geometry an unrestricted view of the treatment site (e.g., of the target area) during monitoring in the two-dimensional (DSA) fluoroscopic image. This may lead to safe and faster treatment. The method may be used to advantage in neurovascular treatments, such as aneurysms, AVMs, and the like. Particularly, minimally invasive interventions are, for example, the insertion of stents, the removal of occlusions, and the like.

The imaging zones may be selected, for example, outside the region of interest. In one embodiment, imaging zones within the region of interest (ROI), depending on size, that is orientated around the target region (and therefore known in the three-dimensional image data set) may be included. For example, however, the region of interest is to be placed closely around the target area, a pathological feature, for example, which may be achieved both manually and at least in some cases automatically. Apart from setting the region of interest, which may include a practitioner's intervention, all the acts in the method according to one or more of the present embodiments are carried out automatically (e.g., by a control device of the X-ray device).

The three-dimensional image data set, which is basically known in the prior art, is acquired next. According to the properties of the X-ray device that is used, a single administration of contrast agent may already be sufficient to acquire all the filled images from the various projection directions. The reconstruction of three-dimensional images from the two-dimensional projection images may be provided using basically known methods, such as filtered back projection and/or iterative reconstruction.

The acquisition of the three-dimensional image data set may take place using the same X-ray device as the fluoroscopic image in the patient who has meanwhile not been moved. The subtraction angiography data set may be acquired before or at the beginning of the interventional procedure (e.g., when the patient is already positioned on a corresponding patient couch). If an X-ray device with adjustable imaging geometries is used (e.g., an X-ray device with a C-arm), this X-ray device may also be used to acquire the projection images underlying the three-dimensional image data set by, for example, the C-arm being swiveled round the patient and the projection images being acquired from different projection directions. If the same X-ray device is now used to acquire the fluoroscopic images and if the patient is essentially not moved, a registration is already available. This provides that the acquisition geometry and the position of the fluoroscopic image in relation to the three-dimensional subtraction angiography image data set are known, such that the forward projection may be carried out without further problems and path information may be transferred onto the fluoroscopic image from the forward projection data set. For the last act mentioned, as is set out in further detail hereinafter, a fine registration may represent a useful expansion. In the control devices of modern C-arm X-ray devices, in most cases, the position of the X-ray source and of the X-ray detector and the orientation thereof are known, such that a practitioner may set a desired imaging geometry. The desired imaging geometry is then also directly known and is available in order to carry out the preliminary calculations for superimposition-free imaging of the target area.

However, a coordinate system may be registered in the X-ray device to acquire fluoroscopic images with the subtraction angiography data set, as is basically known in the prior art. This is, however, less preferable than the use of one and the same X-ray device to acquire the subtraction angiography data set and the fluoroscopic image when the patient has not moved.

Nonetheless, cases frequently occur, in which the patient, at least internally, cannot remain completely motionless, whether this is due to natural, periodic movement in the patient or due to the present embodiments, caused by a medical instrument, for example. In such cases, a useful further development makes provision that, before the acquisition of the pixels that display the image-obscuring blood vessels in the imaging zones, a fine registration of the forward projection data set and of the fluoroscopic image ensues due to at least the path of the image-obscuring blood vessels in the region of interest, as described by the path information. Once, therefore, it is at least partially known what path the image-obscuring blood vessels take, an attempt may be made to locate the image-obscuring blood vessels likewise in the fluoroscopic image and to match image-obscuring blood vessels up (e.g., after an excellent starting position has been provided by the underlying registration). Any 2D-2D-registration methods may be used in order to provide as precise as possible a superimposition. An elastic registration may be provided if, for example, there is the threat of a distortion of blood vessels by medical instruments or such like. By such a refinement of the registration (e.g., fine registration), it is possible to compensate for the effects of smaller movements and the like, such that the quality of the ultimate fluoroscopic image that depicts the target area may again be clearly increased.

In one embodiment, a center line and/or an extent of the image-obscuring blood vessels may be determined as path information. In fact, image evaluation methods for analyzing blood vessels that, for example, provide a center line into which an extent of the blood vessels (e.g., of a radius or a diameter) may be incorporated in each case at the respective points in the center line are already known. After, in most cases, in three-dimensional subtraction angiography data sets, a mostly high quality has been provided by combining the data from many individual projection images, the path may be determined there extremely precisely, described, for example, by a center line and extent. If, in addition, the extent is incorporated into the data structure of the center line, an extremely compact data structure is provided, which is then further easy to handle.

In one embodiment, an extent of the image-obscuring blood vessels that is to be considered when producing the masked image is provided by segmentation of the image-obscuring blood vessels in the fluoroscopic image at least in the region of the interest (e.g., in the context of the fine registration). However, such segmentations may prove to be somewhat more complex due to the superimpositions, such that the excellent information in the three-dimensional image data set may be used.

At this point, the path information for the image-obscuring blood vessels may be defined insofar as the complete path of the image-obscuring blood vessels is provided therein at least also between imaging zones and/or between an imaging zone and the region of interest. Precisely when constant attenuations over the path of the image-obscuring blood vessel have not been assumed and when varying intensity values therefore are to be assumed along the center line in the masked image, it is useful to know the path as fully as possible on the basis of support points.

An advantage of the procedure according to one or more of the present embodiments is that any technically achievable imaging geometry may be handled in the context of the method. This is advantageous if during the interventional procedure (e.g., during the fluoroscopic image monitoring) the imaging geometry is changed. Whilst the forward projection data set may continue to be used for a plurality of fluoroscopic images in the same imaging geometry, in one embodiment, the forward projection data set may be redefined using the new imaging geometry, and in the event of a change in the imaging geometry during the fluoroscopic image monitoring, this forward projection data set may be used for subsequently acquired fluoroscopic images of the new imaging geometry. Once the three-dimensional subtraction angiography image data set continues to be available, the respective image-obscuring blood vessels, superimposition-free imaging zones assigned thereto, and the path information may therefore be defined extremely quickly for newly set imaging geometries, such that even a change in the imaging geometry during image monitoring may be supported.

In a variant, an intensity of the imaging of the image-obscuring blood vessels in the masked image may be determined by interpolation or extrapolation between or from the intensities measured on the pixels in the imaging zones. For example, when it cannot be assumed that the intensity that is created by the attenuation of the image-obscuring blood vessel will remain constant only along this center line, it is useful to interpolate the intensity between the support points provided by the imaging zones or to extrapolate the support points based on the imaging zones towards the region of interest, for which purpose the entire path of the image-obscuring blood vessel is usefully known towards the region of interest. Such intensity fluctuations/attenuation fluctuations may originate from the distribution of the contrast agent in the image-obscuring blood vessels or even from variations in the structure of the image-obscuring blood vessels. It is possible, using the procedure described here, to likewise take into account the resulting effects.

An intensity trajectory acquired along the center line of the image-obscuring blood vessels as part of the path information may be defined by interpolation or extrapolation. The interpolation/extrapolation may therefore essentially take place one-dimensionally along the center line, which considerably simplifies the calculations and supports the real time capabilities of the method according to one or more of the present embodiments. Once the general shape of blood vessels is known, the attenuation path perpendicular to the center lines may easily be estimated. For this purpose, a function that is parameterizable depending on the extent may be used in the masked image to describe the decrease in attenuation towards the edge of the image-obscuring blood vessels. Corresponding models of blood vessels are already known in the prior art and may be used to be able to locate a corresponding appropriate function.

In the context of an interpolation or extrapolation, superimposition-free segments of the image-obscuring blood vessels may be selected as close as possible to the region of interest as imaging zones in the projection direction. In this way, the distance of the support points provided in the interpolation/extrapolation from the region of interest or target area is kept as short as possible.

In addition to the method, one or more of the present embodiments also relate to an X-ray device including a control device configured to carry out the method. All the statements relating to the method according to the present embodiments may likewise be applied by analogy to the X-ray device according to the present embodiments, such that the advantages referred to in the aforementioned may likewise be obtained with the device. For example, the device may be an X-ray device with a C-arm, on which an X-ray beam and an X-ray detector are fixed opposite each other. Such C-arm X-ray devices are used particularly frequently in angiography laboratories for the interventional treatment since there is high flexibility due to the C-arm.

One or more of the present embodiments also relate to a computer program (e.g., including instructions) that carries out the acts in the method according to one or more of the present embodiments when the computer program is run on a computation device (e.g., on the aforementioned control device of the X-ray device). The statements relating to the method and to the X-ray device likewise continue to apply to the computer program. With respect to the acquisition of the three-dimensional subtraction angiography data set and of the fluoroscopic image, the implementation of the acts is to be understood as an activation of the respective components of the X-ray device. The computer program may be stored on a non-transitory, electronically readable data-carrier (e.g., on a CD-ROM).

The control device (e.g., a processor) that, as a computation device, carries out the method may also include, in addition to a control unit to activate components of the X-ray device to acquire X-ray data, a selection unit to select the region of interest, an imaging geometry acquisition unit to acquire the imaging geometry that is currently set, a forward projection data set acquisition unit to acquire the forward projection data set, a masked image acquisition unit to acquire the masked image, and a display unit to display the fluoroscopic image on a display device of the X-ray device.

BRIEF DESCRIPTION OF THE DRAWINGS

FIG. 1 shows a flow chart of an embodiment of a method;
FIG. 2 shows a not yet modified fluoroscopic image;
FIG. 3 shows a modified fluoroscopic image; and
FIG. 4 shows one embodiment of an X-ray device.

DETAILED DESCRIPTION

FIG. 1 shows a flow diagram of an embodiment of a method. This provides image support when monitoring an interventional procedure. In the present image, by way of example, a minimally invasive, neurovascular intervention may be observed.

In act S1, before the start of the intervention or at the start thereof, a three-dimensional subtraction angiography image data set of the vascular system of the patient awaiting treatment that contains the target region is acquired. For this purpose, therefore, masked projection images and filled projection images are acquired from different projection directions. From these images, including a reconstruction, a three-dimensional subtraction angiography image data set may be acquired in one of the known ways.

In act S2, a region of interest within the subtraction angiography image data set that surrounds (e.g., closely surrounds) the target region is established either automatically and/or manually. The target region may, for example, be marked by a user using a corresponding user interface, whereupon a region of interest (ROI) is placed a certain distance around the target area.

In act S3, an imaging geometry, including a projection direction, that is intended to be used to acquire fluoroscopic images for image monitoring of the intervention during the intervention is defined. The fluoroscopic images are to be acquired using the same X-ray device as the three-dimensional image data set. If the user has set a desired imaging geometry, this is known in the control device of the X-ray device that carries out the method described here. The corresponding adjustable components therefore supply corresponding feedback to the control device.

In act S4, a two-dimensional forward projection data set relating to the currently selected imaging geometry is acquired. Once the same X-ray device has been used to acquire both the fluoroscopic images and the subtraction angiography data set, and the patient has essentially not moved, the relationship of the imaging geometry to the subtraction angiography data set is known, such that an acquisition may be simulated in the sense of a forward projection. For example, it is first determined at this point which blood vessels in fluoroscopic images of the imaging geometry will superimpose the target area in an image-obscuring manner. These are referred to hereinafter as image-obscuring blood vessels. This therefore provides that, in the case of image-obscuring blood vessels, beam trajectories through the target area also pass through the image-obscuring blood vessel. Instead of observing the target area alone, the entire region of interest may be observed here if this simplifies the calculations. Once the image-obscuring blood vessels have been identified, it is likewise possible to determine, based on the known imaging geometry and the forward projection, where the image-obscuring blood vessels are displayed outside the region of interest without any superimpositions (e.g., exclusively). Such zones that are superimposition-free with respect to the image-obscuring blood vessels are referred to as imaging zones and are stored. In the present case, what are selected as imaging zones are such regions that depict the image-obscuring blood vessels without any superimposition, and which are as close as possible to the target area or region of interest. The two-dimensional path of the image-obscuring blood vessels in the forward projection is determined in the imaging zones and in the region of interest and stored as path information along with the position of the imaging zones and the region of interest in the forward projection data set. In the present case, the center line and the extent of the image-obscuring blood vessels are acquired. The extent may be encoded into a data structure of the center line in order to allow as compact as possible storage of the data.

In act S5, there then ensues the acquisition of a two-dimensional fluoroscopic image, often triggered by the activation of a foot pedal by a person carrying out or involved in the intervention. The two-dimensional fluoroscopic image is a two-dimensional subtraction angiography image. This provides that a filled image is measured by the X-ray device. From this image, a masked image is subtracted in order to acquire the fluoroscopic image.

FIG. 2 shows such a fluoroscopic image 1 in diagram form and purely by way of example. The target area 2 (e.g., an aneurysm) is located along a blood vessel 3. It is evident that the region of interest indicated 4 really closely surrounds the target area 2. The view of the target area 2 is, however, superimposed by image-obscuring blood vessels 5, 6 that make it more difficult to estimate the target area. The acts that follow make use of the two-dimensional forward projection data set from act S4 in order to remove, in the region of interest 4, the representation of the image-obscuring blood vessels 5, 6 that are not in direct contact with the target area 2.

In an optional act S6, first a fine registration takes place (e.g., a refinement of the already existing registration), which provides that the path information is used to match up the fluoroscopic image 1 and the two-dimensional forward projection data set as precisely as possible. In this way, smaller movements by the patient and/or changes due to the use of a medical instrument may be compensated for.

Act S7 then serves for the acquisition of a masked image of the region of interest. The path of the image-obscuring blood vessels 5, 6 inside the region of interest 4 is already known from the path information. For a masked image in order to fill a corresponding representation of the image-obscuring blood vessels 5, 6 in the region of interest 4 with intensity values, the imaging zones are used. From the imaging zones and the registration that is available, the pixels in the fluoroscopic image 1 on which the respective image-obscuring blood vessel 5, 6 is represented without any superimposition are ultimately known. This provides that the intensity values contained therein in the fluoroscopic image originate only from the effect of the attenuation of the corresponding image-obscuring blood vessel 5, 6. The corresponding intensity values in the imaging zones, observed along the center line, now represent support points in order to determine, by the path information, intensity values for imaging of the image-obscuring blood vessels 5, 6 that is not considered to be superimposed even inside the region of interest 4. In one embodiment, a linear interpolation may take place between the adjacent imaging zones opposite the region of interest, but even more complex approaches may be adopted. Should an imaging region be present on only one side of the region of interest 4, which is less preferable, an extrapolation may likewise ensue.

After the interpolation, an intensity trajectory along the center line of the image-obscuring blood vessels 5, 6, for example, is also known within the region of interest 4. The trajectory is now used where the image-obscuring blood vessels 5, 6 appear in the region of interest 4 to fill the masked image with intensity values that display the attenuation fraction thereof. In this case, the attenuation fractions with image-obscuring blood vessels 5, 6 that are superimposed one over the other are cumulated accordingly. In order to be able to reproduce the intensity trajectory as correctly as possible even towards the edge of the image-obscuring blood vessels 5, 6, the corresponding intensity value in the masked image decreases according to a function that is based on a blood vessel model. The function is parameterized with the respective extensions.

The resulting masked image therefore contains precisely and exclusively the contribution due to the image-obscuring blood vessels 5, 6 within the region of interest 4.

In act S8, the masked image in the region of interest 4 is subtracted from the fluoroscopic image 1, such that a corrected fluoroscopic image 1' is generated, as indicated by FIG. 3. As shown in FIG. 3, the contributions due to the image-obscuring blood vessels 5, 6 within the region of interest 4 have been removed, such that an undistorted view of the target area 2 is provided. Likewise, according to the method, see FIG. 1, in act S9, the fluoroscopic image is shown on a display device of the X-ray device.

In act S10, a check is carried out to see whether the imaging geometry is changing. If this is not the case, then the procedure continues again as usual with the acquisition of the next fluoroscopic image with act S5. The forward projection data set therefore remains unchanged. If the imaging geometry changes, however, because, for example, the target area 2 is to be considered from a different perspective, the new imaging geometry is defined according to act S3, and a new forward projection data set is acquired accordingly for the imaging geometry in act S4. The data set is then used accordingly to modify the fluoroscopic image 1 in order to remove the fractions due to the image-obscuring blood vessels 5, 6.

FIG. 4 shows a sketch illustrating the principles of an X-ray device 7 according to one or more of the present embodiments. The X-ray device 7 includes a C-arm 8, on which an X-ray source 9 and an X-ray detector 10 are arranged opposite each other. Thanks to the movability of the C-arm 8, different imaging geometries relating to a patient (not shown here) placed on a patient couch 11 may be set. The X-ray device 7 further includes a control device 12 that is configured to carry out the method according to one or more of the present embodiments. The X-ray device 7 also includes a display device 13 (e.g., a monitor) to display the modified fluoroscopic image 1'.

Although the invention has been illustrated and described in greater detail with the embodiments, the invention is not restricted to the examples disclosed. Other variants may be derived therefrom by a person skilled in the art without going beyond the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing image support to a practitioner in an interventional treatment of a target area in a patient, the method comprising:
    acquiring a three-dimensional (3D) subtraction angiography image data set including a target region of the patient that includes the target area;
    selecting a region of interest in the 3D subtraction angiography image data set, the region including the target area;
    defining an imaging geometry that implements a projection direction for acquiring two-dimensional (2D) fluoroscopic images for monitoring the intervention using an X-ray device;
    determining image-obscuring blood vessels that superimpose the region of interest in the imaging geometry, and determining imaging zones that show fractions of the image-obscuring blood vessels in the imaging geometry without superimposition by other blood vessels by forward projection of the 3D subtraction angiography image data set in the projection direction;
    defining path information relating to the image-obscuring blood vessels at least in a zone around the region of interest and in the imaging zones, and inputting the path information into a 2D forward projection data set;
    acquiring a fluoroscopic image in the imaging geometry;
    determining pixels that show the image-obscuring blood vessels in the fluoroscopic image using the information relating to the path, and determining image intensity information from intensities measured on pixels in the fluoroscopic image;
    modifying the fluoroscopic image, the modifying comprising subtracting a masked image of the image-obscuring blood vessels acquired by the path information in the region of interest and the image intensity information from the fluoroscopic image in the region of interest; and
    displaying the modified fluoroscopic image.

2. The method of claim 1, wherein acquiring the 3D subtraction angiography image data set ensues with the same X-ray device as the fluoroscopic image in the patient, the patient not being moved between the acquiring of the 3D subtraction angiography image data set and the acquiring of the fluoroscopic image, or a coordinate system of the X-ray device is or becomes registered with the subtraction angiography data set in order to acquire the fluoroscopic images.

3. The method of claim 1, wherein before the determining of the image-obscuring blood vessels in the pixels showing the imaging zones, a fine registration of the 2D forward projection data set and of the fluoroscopic image ensues based on at least the path of the image-obscuring blood vessels in the region of interest described by the information relating to the path.

4. The method of claim 1, wherein the path information includes at least a center line, an extent, or the center line and the extent of the image-obscuring blood vessels, an extent of the image-obscuring blood vessels that is to be considered when generating the masked image in the fluoroscopic image is determined at least in the region of interest, or a combination thereof.

5. The method of claim 1, wherein when there is a change in the imaging geometry during fluoroscopic image monitoring, the method further comprises providing a fresh definition of the 2D forward projection data set using the new imaging geometry, and subsequently using the forward projection data set to correct fluoroscopic images of the new imaging geometry.

6. The method of claim 1, wherein an intensity of the imaging of the image-obscuring blood vessels in the masked image is acquired by interpolation or extrapolation between or from intensities measured on the pixels in the imaging zones.

7. The method of claim 6, wherein through the interpolation or extrapolation, an intensity trajectory is defined along the center line of the image-obscuring blood vessels that has been acquired as part of the path information.

8. The method of claim 7, wherein a function that is parameterizable according to the extent is used in the masked image towards an edge of the image-obscuring blood vessels to describe a decrease in an attenuation described by the intensity.

9. The method of claim 6, wherein superimposition-free segments of the image-obscuring blood vessels are selected as imaging zones in the projection direction as close as possible to the region of interest.

10. The method of claim 4, wherein the extent of the image-obscuring blood vessels that is to be considered when generating the masked image in the fluoroscopic image is determined at least in the region of interest in the context of the fine registration.

11. An X-ray device comprising:
a controller configured to:
acquire a three-dimensional (3D) subtraction angiography image data set including a target region of a patient that includes a target area;
select a region of interest in the 3D subtraction angiography image data set, the region of interest including the target area;
define an imaging geometry that implements a projection direction for acquiring two-dimensional (2D) fluoroscopic images for monitoring the intervention using an X-ray device;
determine image-obscuring blood vessels that superimpose the region of interest in the imaging geometry, and determining imaging zones that show fractions of the image-obscuring blood vessels in the imaging geometry without superimposition by other blood vessels by forward projection of the 3D subtraction angiography image data set in the projection direction;
define path information relating to the image-obscuring blood vessels at least in a zone around the region of interest and in the imaging zones, and inputting the path information into a 2D forward projection data set;
acquire a fluoroscopic image in the imaging geometry;
determine pixels that show the image-obscuring blood vessels in the fluoroscopic image using the information relating to the path, and determining image intensity information from intensities measured on pixels in the fluoroscopic image;
modify the fluoroscopic image, the modifying comprising subtracting a masked image of the image-obscuring blood vessels acquired by the path information in the region of interest and the image intensity information from the fluoroscopic image in the region of interest; and
display the modified fluoroscopic image.

12. In a non-transitory computer-readable storage medium that stores instructions executable by a computer to provide image support to a practitioner in an interventional treatment of a target area in a patient, the instructions comprising:
acquiring a three-dimensional (3D) subtraction angiography image data set including a target region of the patient that includes the target area;
selecting a region of interest in the 3D subtraction angiography image data set, the region including the target area;
defining an imaging geometry that implements a projection direction for acquiring two-dimensional (2D) fluoroscopic images for monitoring the intervention using an X-ray device;
determining image-obscuring blood vessels that superimpose the region of interest in the imaging geometry, and determining imaging zones that show fractions of the image-obscuring blood vessels in the imaging geometry without superimposition by other blood vessels by forward projection of the 3D subtraction angiography image data set in the projection direction;
defining path information relating to the image-obscuring blood vessels at least in a zone around the region of interest and in the imaging zones, and inputting the path information into a 2D forward projection data set;
acquiring a fluoroscopic image in the imaging geometry;
determining pixels that show the image-obscuring blood vessels in the fluoroscopic image using the information relating to the path, and determining image intensity information from intensities measured on pixels in the fluoroscopic image;
modifying the fluoroscopic image, the modifying comprising subtracting a masked image of the image-obscuring blood vessels acquired by the path information in the region of interest and the image intensity information from the fluoroscopic image in the region of interest; and
displaying the modified fluoroscopic image.

13. The non-transitory computer-readable storage medium of claim 12, wherein acquiring the 3D subtraction angiography image data set ensues with the same X-ray device as the fluoroscopic image in the patient, the patient not being moved between the acquiring of the 3D subtraction angiography image data set and the acquiring of the fluoroscopic image, or a coordinate system of the X-ray device is or becomes registered with the subtraction angiography data set in order to acquire the fluoroscopic images.

14. The non-transitory computer-readable storage medium of claim 12, wherein before the determining of the image-obscuring blood vessels in the pixels showing the imaging zones, a fine registration of the 2D forward projection data set and of the fluoroscopic image ensues based on at least the path of the image-obscuring blood vessels in the region of interest described by the information relating to the path.

15. The non-transitory computer-readable storage medium of claim 12, wherein the path information includes at least a center line, an extent, or the center line and the extent of the image-obscuring blood vessels, an extent of the image-obscuring blood vessels that is to be considered when generating the masked image in the fluoroscopic image is determined at least in the region of interest, or a combination thereof.

16. The non-transitory computer-readable storage medium of claim 12, wherein when there is a change in the imaging geometry during fluoroscopic image monitoring, the instructions further comprise providing a fresh definition of the 2D forward projection data set using the new imaging geometry, and subsequently using the forward projection data set to correct fluoroscopic images of the new imaging geometry.

* * * * *